United States Patent [19]

Rayhack

[11] Patent Number: 4,929,247
[45] Date of Patent: May 29, 1990

[54] BONE COMPRESSION AND DISTRACTION DEVICE

[76] Inventor: John M. Rayhack, 13919 Shady Shores Dr., Tampa, Fla. 33613

[21] Appl. No.: 254,158

[22] Filed: Oct. 6, 1988

[51] Int. Cl.⁵ ............................................. A61F 2/00
[52] U.S. Cl. ..................................... 606/53; 606/105
[58] Field of Search ............ 128/92 R, 92 Z, 92 ZZ, 128/92 ZY, 92 ZK, 92 ZW, 92 YP, 92 YL, 92 YF, 92 VY; 606/105, 53

[56] References Cited

U.S. PATENT DOCUMENTS

| Re. 31,809 | 1/1985 | Danieletto | 128/92 ZZ |
|---|---|---|---|
| 1,789,060 | 1/1931 | Weisenbach | 128/92 Z |
| 2,434,431 | 1/1948 | Pincock | 128/92 Z |
| 3,244,170 | 4/1966 | McElvenny | 128/92 YP |
| 3,386,437 | 6/1968 | Treace | 128/92 YP |
| 3,400,711 | 9/1968 | Hux | 128/92 YP |
| 3,547,113 | 12/1970 | Swanson | 128/92 ZY |
| 3,604,414 | 9/1971 | Borges | 128/92 YL |
| 3,709,219 | 1/1973 | Halloran | 128/92 ZZ |
| 3,900,025 | 8/1975 | Barnes | 128/92 YL |
| 3,993,055 | 11/1976 | Volkov | 128/92 ZZ |
| 4,096,857 | 6/1978 | Cramer | 128/92 ZY |
| 4,187,841 | 2/1980 | Knutson . | |
| 4,570,625 | 2/1986 | Harris | 128/92 ZZ |
| 4,621,627 | 11/1986 | DeBastiani | 128/92 ZZ |

FOREIGN PATENT DOCUMENTS

| 0073455 | 3/1986 | European Pat. Off. | 128/92 ZZ |
|---|---|---|---|
| 0373516 | 1/1964 | Switzerland | 128/92 YP |
| 0305883 | 8/1971 | U.S.S.R. | 128/92 ZZ |
| 0402364 | 3/1974 | U.S.S.R. | 128/92 ZZ |
| 0197709 | 11/1977 | U.S.S.R. | 128/92 Z |
| 0891085 | 12/1981 | U.S.S.R. | 128/92 Z |
| 0952238 | 8/1982 | U.S.S.R. | 128/92 Z |

OTHER PUBLICATIONS

Salenius, Pentti, "The Journal of Bone and Joint Surgery", Mar. 1970, vol. 52A, No. 2, pp. 328-383.

Primary Examiner—Robert A. Hafer
Assistant Examiner—Michael Brown
Attorney, Agent, or Firm—Dominik, Stein, Saccocio, Reese, Colitz & Van Der Wall

[57] ABSTRACT

A bone compression and distraction device for compressing and distracting the ends of a bone and affixing a splint plate thereacross. The device comprises a pair of blocks interconnected by an adjustment assembly. The blocks are each seated on the ends of the splint plate and connected to the respective ends of the bone by a long bone screw positioned through a transverse hole in the block and through aligned holes in the splint plate. One of the holes in the splint plate is slotted to allow the compression or distraction of the bone ends whereupon short bone screws are positioned through other holes in the splint plate into the bone ends allowing the blocks to be removed and its screws replaced by short bone screws positioned through the same holes in the plate and into the bone ends.

12 Claims, 3 Drawing Sheets

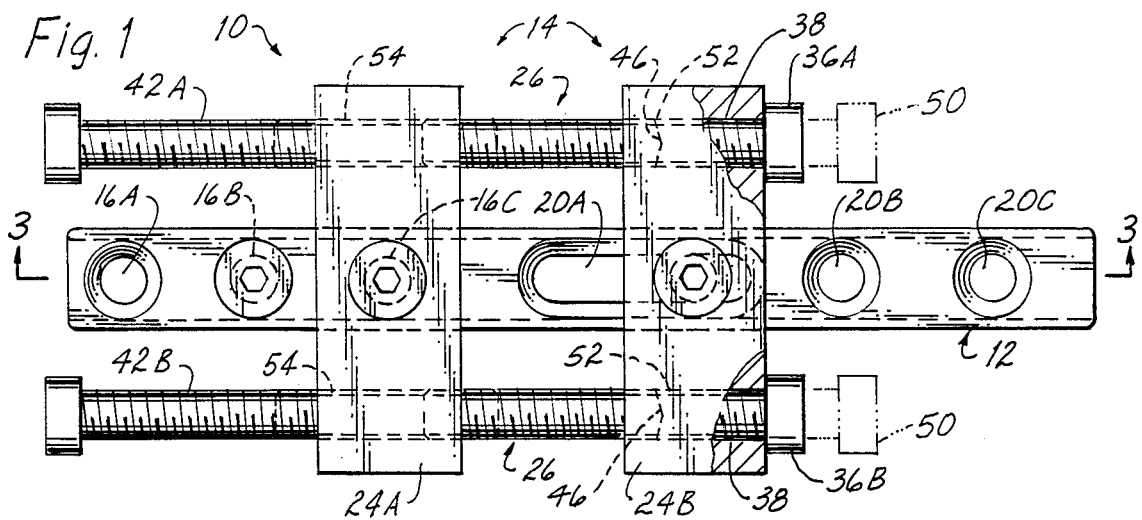
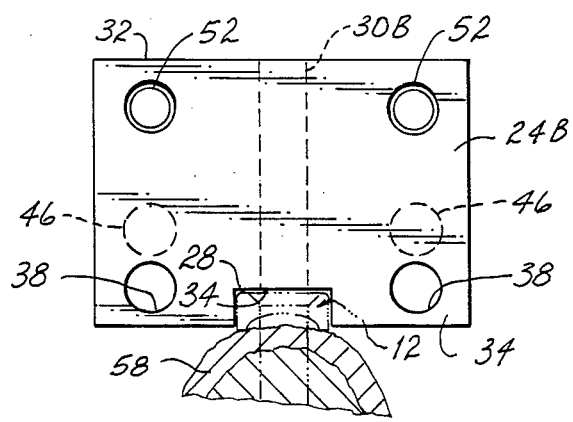
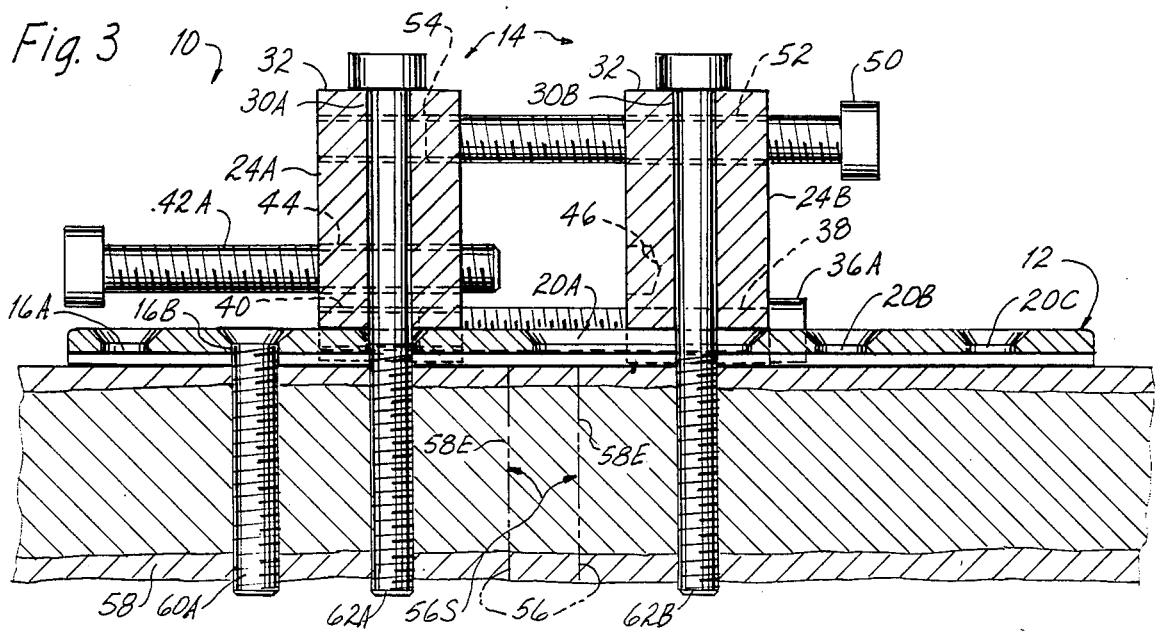

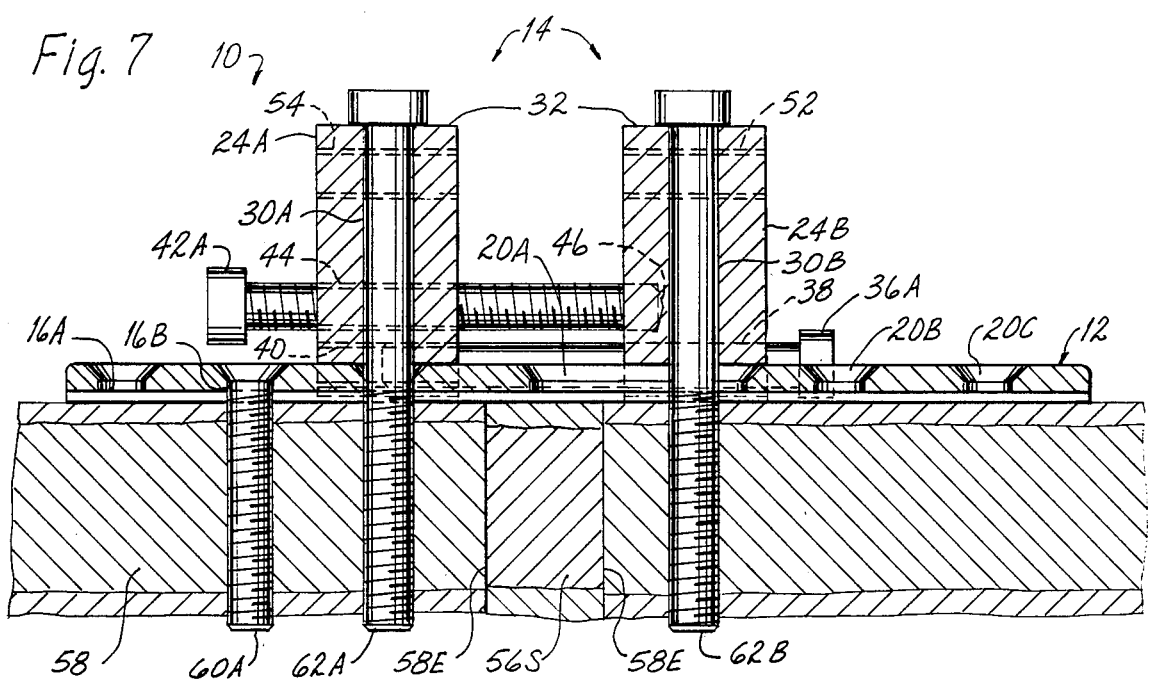

BONE COMPRESSION AND DISTRACTION DEVICE

BACKGROUND OF THE INVENTION

1. Field of the Invention

This invention relates to bone compression and distraction devices designed to compress or distract the ends of a fractured or cut bone. More particularly, this invention relates to bone compression and distraction devices which utilize an adjustment assembly in combination with a slotted plate.

2. Description of the Background Art

Presently, there exist numerous types of bone compression devices in which the ends of a fractured or cut bone are forced together by an adjustment assembly whereupon a permanent or temporary internal splint bar is affixed to securely retain the ends of the bone together. There also exist numerous types of bone distraction devices which allow a bone to be lengthened by cutting the bone and distracting the ends of the bones apart by the desired distance, affixing the ends in place with a permanent or temporary internal splint and filling the gap between the plated bone ends with a bone segment to facilitate growth across the spanned distance. Many devices are designed to be used both as a compression and a distraction device. U.S. Pat. Nos. 3,244,170, 3,604,414, 4,475,546, 4,187,841, 3,709,219, 2,333,033, EU No. 747,876, DL No. 206,074 and FR. No. 1,507,627 disclose various embodiments of bone compression and distraction devices.

East German Patent No. 206,074 and French patent No. 1,507,627 each disclose a bone compression device including an adjustment assembly designed to be used in combination with a slotted plate. More particularly, the adjustment assembly comprises a stationary block and a moveable block interconnected by a threaded adjustment. The slotted plate includes a pair of screw holes at one end and a slot at another screw hole at the other end. Screws are placed through the pair of screw holes to rigidly affix the one end of the plate to one end of the bone. The stationary block of the adjustment assembly is affixed to the one end of the plate and the moveable block is affixed to the bone at the other end of the plate through the slot either by means of a pin inserted through the slot into the end of the bone (French patent) or by means of a claw which engages the head of a screw positioned through the slot and into the end of the bone (German Patent). Operation of the threaded adjustment of the adjustment assembly causes the moveable block to slide toward the stationary block thereby compressing the ends of the bone together. Once compressed, screws are positioned in the screw hole and the slot at the other end of the plate, thereby rigidly securing the ends of the bone together.

U.S. Pat. No. 3,244,170 discloses a similar bone compression device including a tension device for use in combination with a slotted plate. In this patent, the slotted plate includes a slot at both of its ends through which screws are inserted for threaded engagement with the respective ends of the bone. The adjustment assembly engages the heads of the screws and, upon operation, forces the screws together thereby compressing the ends of the bone together. Once compressed, permanent screws are inserted into screw holes in the plate while the adjustment assembly retains the ends of the bone under compression. After the screws are securely tightened, the adjustment assembly is removed.

Several disadvantages are noted with respect to the above referenced bone compression and distraction devices. First, the patents referenced above illustrate the bone screws engaging through only one cortex of the bone. Further, the adjustment assembly is positioned substantially off axis from the axis of the bone being compressed or distracted. Thus, an excessive force is exerted by the adjustment assembly which may result in the bending of the bone screw or toggling of the bone screw in the bone thereby weakening the connection of the adjustment assembly to the bone under compression or distraction. Additionally, the adjustment assembly's use of a pin (French Patent) or a claw (German Patent) may result in scoring of the slotted plate should the pin or claw slip during use. The scoring of the plate could then result in crevice corrosion.

Finally, some of the devices disclosed above do not provide for both compression and distraction of a bone. Without both features, the difficulty of inserting a bone segment during the lengthening of the bone is increased since the ends of the bone cannot be compressed to retain the bone segment therebetween. Additionally, recutting or reshaping of the ends of the bones is not easily accomplished without both features of both distraction and compression.

Therefore, it is an object of this invention to provide an apparatus which overcomes the aforementioned inadequacies of the prior art devices and provides an improvement which is a significant contribution to the advancement of the bone distraction and compression art.

Another object of this invention is to provide a new and improved bone compression and distraction device including an adjustment assembly designed for use in combination with a slotted plate, the device operable as a compression device and/or a distraction device.

Another object of this invention is to provide a bone compression or distraction device including a slotted plate and an adjustment assembly, the adjustment assembly having a stationary block and a moveable block interconnected by a threaded adjustment, the blocks having a transverse hole allowing bone screws to be inserted therethrough and then through a hole and a slot, respectively, in the slotted plate for threading into the respective ends of the bone thereby minimizing the inadvertent scoring of the slotted plate.

Another object of this invention is to provide a bone compression or distraction device including an adjustment assembly which produces a compressive or distractive force adjacent to the axis of a bone being compressed or distracted, thereby minimizing bending, toggling, or otherwise weakening of the bone screws in the bone.

Another object of this invention is to provide a bone compression or distraction device which allows the removal of a segment of bone from a long bone of the forearm (ulna) while being held in original rotational orientation by means of a slotted plate and which can then be operated to compress the two ends of the bone together to then be held in place by means of additional bone screws positioned through the plate, thereby shortening the entire length of the bone.

The foregoing has outlined some of the more pertinent objects of the invention. These objects should be construed to be merely illustrative of some of the more prominent features and applications of the intended invention. Many other beneficial results can be obtained by applying the disclosed invention in a different manner or modifying the invention within the scope of the disclosure. Accordingly, other objects and a fuller understanding of the invention may be had by referring to the summary of the invention and the detailed description of the preferred embodiment in addition to the scope of the invention defined by the claims taken in conjunction with the accompanying drawings.

SUMMARY OF THE INVENTION

The invention is defined by the appended claims with a specific embodiment shown in the attached drawings. For the purpose of summarizing the invention, the invention comprises a bone compression and distraction device having an adjustment assembly and a slotted plate. More particularly, the slotted plate includes a pair of holes at one end and a slot and another hole at its other end. The adjustment assembly comprises two jaws or blocks adjustably interconnected by means of a threaded adjustment such as screws. The axis of the threaded adjustment is substantially adjacent to the axis of the bone. Each block includes a transverse hole allowing a bone screw to be inserted therethrough in diametrical alignment with the bone. Each block further includes a longitudinal indentation allowing the block to be seated over the plate with the axis of the transverse holes parallel or colinear to the axes of the holes and slot in the plate.

The bone compression and distraction device may be used as a compression device to allow the removal of a segment of bone from a long bone, such as the ulna. Specifically, the bone may be cut approximately one-half to three-quarters of the way through at the site where the bone segment is to be removed. The plate is then positioned over the cut. One of the blocks (hereinafter referred to as the stationary block) is seated over the plate with its transverse hole in colinear alignment with one of the screw holes in the one end of the plate. A hole is drilled and tapped in the bone and then a bone screw is inserted through the transverse hole, through the hole in the plate and diametrically through both cortices of the bone, thereby rigidly securing the stationary block and plate into position at one end of the bone. The other block (hereinafter referred to as the moveable block) is seated over the far area of the slot in the other end of the plate whereupon a bone screw is inserted through its transverse hole through the slot and diametrically into previously drilled and tapped holes in the two cortices of the bone.

After the bone screws are tightened, the bone cuts are cut fully through allowing the bone segment to be removed. It is noted that the plate prevents rotational movement of the ends of the bone relative to one another. The transverse bone screw in the moveable block may then be slightly loosened allowing it to more easily slide within the slot.

Operation of the threaded adjustment interconnecting the blocks forces the moveable block to move toward the stationary block with its bone screw sliding within the slot in the plate. When the ends of the bone are compressed as desired, bone screws are inserted in the other hole in each end of the plate to rigidly secure the ends of the bone into position. The blocks are removed by unthreading the bone screws positioned in their transverse holes. Shorter bone screws are then threaded into the slot in one end of the plate and another in the other screw hole in the other end of the plate, such that each end of the bone is securely held into position by two bone screws.

The bone compression and distraction device may also be used as a distraction device allowing the insertion of a segment of bone within a bone to lengthen its overall length. More particularly, as in the compression method described above, the bone is cut partially through and, the blocks and plate are rigidly attached by means of bone screws extending through the transverse holes of the block. After the bone is cut fully through, the threaded adjustment is operated to force the moveable block away from the stationary block by a desired distance. A bone segment taken from another bone is then positioned between the ends of the bone. The bone segment may then be compressed between the ends of the bone by operation of the compression feature of the device. Additional bone screws are inserted through the plate and threaded into both cortices of the bone. The blocks are then removed by removal of the transverse screws and replaced by shorter bone screws.

An important feature of this invention is the secure attachment of the blocks to the respective ends of the bone by means of bone screws which extend through transverse holes positioned in each block and which are diametrically threaded into both cortices of the bone itself. A more rigid connection of the blocks to the respective ends of the bone is obtained. Furthermore, the positioning of the bone screws transversely through the blocks results in a more compact type of adjustment assembly which allows more freedom within the confines of the operating site, while minimizing inadvertent scoring of the plate.

Another important feature of this invention is the positioning of the axis of the threaded adjustment to be substantially parallel and adjacent to the axis of the bone. This close positioning of the threaded adjustment reduces the bending, toggling or otherwise weakening of the bone screws which rigidly secure the plate to the bone.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a fuller understanding of the nature and objects of the invention, reference should be had to the following detailed description taken in connection with the accompanying drawings in which:

FIG. 1 is a plan view of the bone compression and distraction device of the invention illustrating the tensioning device thereof seated over the slotted plate in position for use as a compression device;

FIG. 2 is a right end view of FIG. 1 with the positioning and compression screws removed illustrating the indentation formed in the bottom of the blocks of the adjustment assembly for seating on the slotted plate and illustrating the axis of the holes for the distraction and compression screws substantially adjacent to the axis of the slotted plate;

FIG. 3 is a cross sectional view of FIG. 1 along lines 3—3 illustrating the bone segment to be removed;

FIG. 7 is still another cross sectional view of the bone compression and distraction device functioning as a bone distractor illustrating the final position of the blocks of the adjustment assembly after lengthening of the bone.

Similar reference characters refer to similar parts throughout the several views of the drawings.

DETAILED DESCRIPTION OF THE PREFERRED EMBODIMENT

Figure 4:
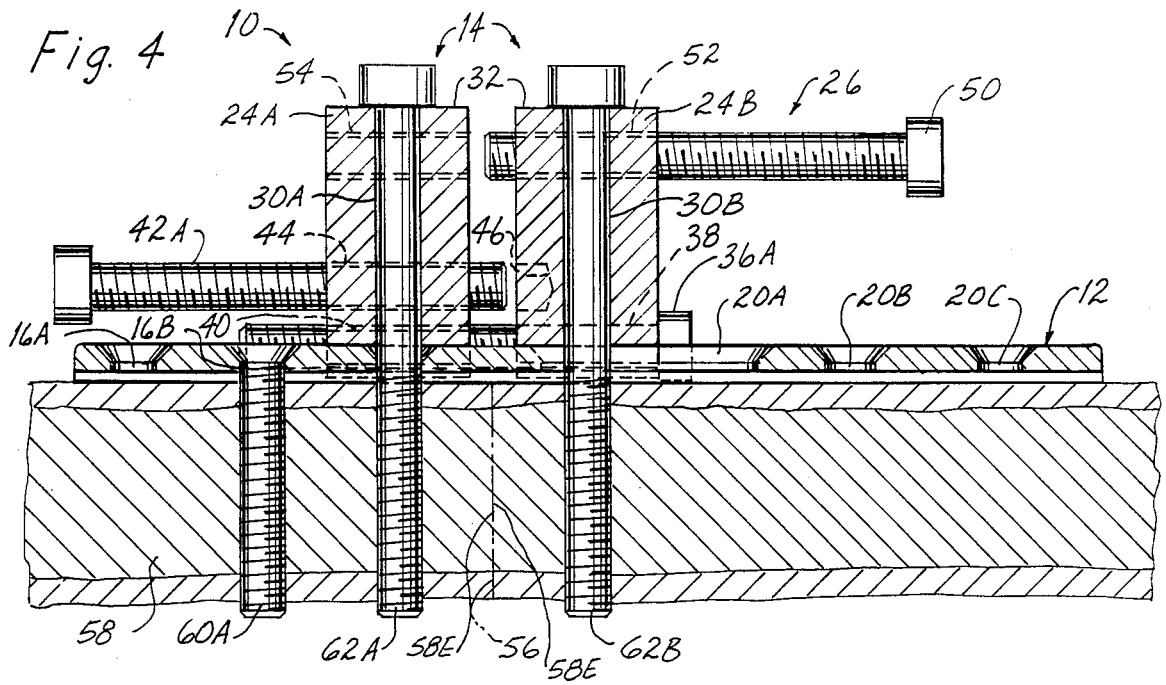
FIG. 4 is another plan view of the bone compression and distraction device illustrating the positioning of the blocks after the bone segment has been removed.

Referring to FIG. 1, the compression and distraction device 10 of the invention comprises a slotted plate and a tensioning assembly, generally indicated by numerals 12 and 14, respectively. More particularly, the slotted plate 12 comprises two or more holes 16A, 16B and 16C in one end 18. Similarly, the slotted plate 12 includes two or more holes 20A, 20B and 20C positioned at the other end 22. Hole 20A comprises a slotted hole.

The tensioning assembly 14 of the compression and distraction device 10 of the invention comprises a pair of blocks 24A and 24B and an adjustment means, generally indicated by numeral 26, which adjustably interconnects the blocks 24.

As shown in FIG. 2, each of the blocks 24 comprises an indentation 28 having a cross sectional configuration similar to the cross sectional configuration of the slotted plate 12 allowing the blocks 24 to be seated thereon. Indentation 28 also functions to center the blocks 24 relative to the plate 12.

As shown in FIG. 3, each of the blocks 24 further include a transverse holes 30A and 30B positioned transversely through the block 24 from the upper surface 32 to the lower surface 34 thereof. It is noted that the axis of each of the transverse holes 30A and 30B is colinear or parallel to the axis of the holes 16 and 20 in the plate 12.

The tensioning assembly 14 comprises a pair of compression screws 36A and 36B which are slidably inserted through an unthreaded hole 38 in one of the blocks (block 24B illustrated) for engagement with a threaded hole 40 in the other block (block 24A illustrated). Thus, it can be readily appreciated that rotation of the compression screws 36 forces the block 24B to move toward block 24A. As best shown in FIG. 2, the axis of the compression screws 36 are preferably substantially adjacent to the longitudinal axis of the plate 12 positioned substantially therebetween.

Figure 6:
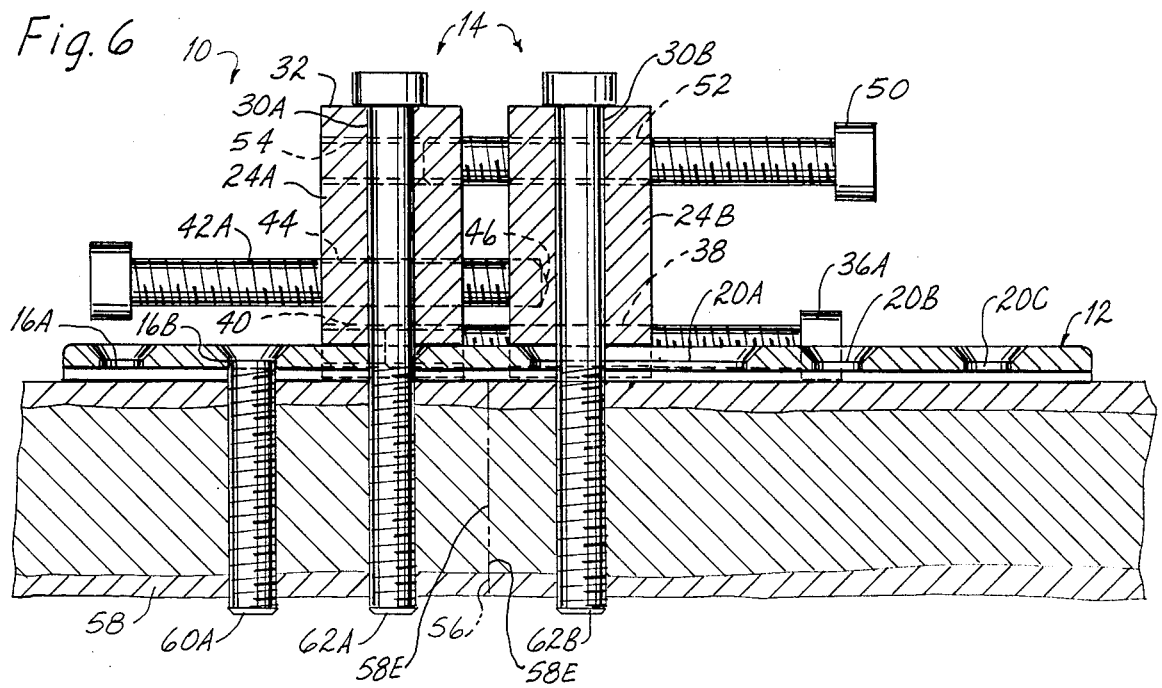
FIG. 6 is another cross sectional view of the bone compression and distraction device of the invention functioning as a distraction device in which a bone is cut through and then extended for lengthening.

As shown in FIG. 6, the tensioning assembly 14 further comprises a pair of distraction screws 42A and 42B which engage through a threaded hole 44 in one of the blocks (block 24A illustrated) to seat into a blind hole 46 positioned in the other block (block 24B illustrated). Rotation of the distraction screws 42 forces the block 24B to move away from block 24A. The axis of the distraction screws 42 are preferably substantially adjacent to axis of the plate 12 positioned substantially therebetween.

As shown in FIGS. 3 and 6, the compression and distraction device 10 of the invention further comprises means for temporarily positioning the blocks 24 in a spaced apart position. More particularly, blocks 24 may be temporarily positioned apart by threading a screw 50 through a threaded hole 52 and 54 in each of the blocks 24. Thus, while positioning screw 50 threadably engages each of the threaded holes 52 and 54, the blocks 24 are held apart at a fixed distance, and can be removed once the transverse screws are inserted into the device and the bone.

The compression and distraction device 10 is utilized as a compression device as follows. As best shown in FIGS. 1 and 3, the plate 12 is positioned over previously formed partial cuts 56 in the bone 58. A bone screw 60A is inserted through hole 16B into a previously drilled and tapped hole in both cortices of the bone 58. Longer bone screws 62 are inserted through the transverse holes 30A and 30B of each block 24A and 24B to engage through holes 16A and 20A, respectively, of the slotted plate 12 into previously drilled and tapped holes in the bone 58.

During the above initial set up procedure, it is noted that the plate 12 is utilized as a guide for the positioning of the holes in the bone 58. It is also noted that the positioning screws 50 may be utilized to facilitate proper positioning of the block 24B relative to the slot hole 20A and specifically, the positioning of block 24B in the far end of the slotted hole 20A (see FIG. 3).

After the initial set up procedure, the positioning screws 50A and B are removed or backed off to the position shown in FIG. 4. The partial cuts 56 in the bone are cut fully through to remove the bone segment 56S (see FIG. 3). The compression screws 36A and 36B may then be rotated by the use of an allen wrench or other tool to gradually force the block 24B toward block 24A until the ends 58E of the bone 58 are compressed together. It is noted that the transverse bone screw 62B may be slightly loosened to allow the screw bone to more freely move within the slotted hole 20A and to allow the bone end 58E to slide under the plate 12.

After compression of the bone ends 58E as shown in FIG. 4, another bone screw 64 is inserted through hole 20B into a previously drilled and tapped hole in both cortices of the bone. Transverse bone screws 62A and 62B may then be unthreaded to remove the blocks 24A and 24B from the plate 12. The transverse bone screws 62A and B are then replaced with shorter bone screws 66A and B (see FIG. 5).

Figure 5:
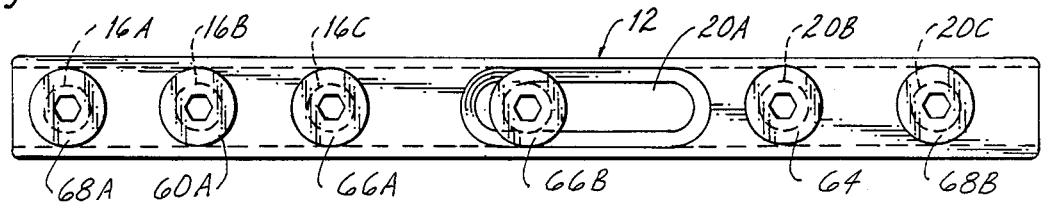
FIG. 5 is a plan view of the slotted splint plate after the blocks have been removed and the additional bone screws have been installed.

As described, the plate 12 is rigidly secured to each end 58E of the bone by at least two bone screws; however, as shown in FIG. 5, additional bone screws 68A and B may be inserted through holes 16A and 20C in the plate 12 through additional previously drilled and tapped holes in both cortices of the bone 58.

Referring to FIGS. 6–7, the compression and distraction device 10 may also be used as a distraction device as follows. The positioning screws 50A and B are used to position the block 24B over the closer end of slot 20A. The plate 12 and the blocks 24A and B of the adjustment assembly 14 are then securely attached to the bone 58 by transverse screws 30A and B and bone screw 60A to straddle a previously formed partial cut 56 in the bone 58.

After initial set-up, positioning screws 50A and B are backed off or removed (see FIG. 7). The cut 56 in the bone 58 is then completed fully through the bone 58. The distraction screws 42A and B are rotated to force the block 24B away from block 24A by the desired distance. It is noted that the separation distance may be gauged by measuring the distance between the blocks 24A and B during distraction.

Once distracted, a bone segment 56S is inserted between the bone ends 58E (see FIG. 7). The distraction screws 42A and B are backed off and the compression screws 36A and B are installed. The compression screws 36A and B of the adjustment assembly 14 may then be rotated to slightly compress the bone segment 56S between the bone ends 58E. The blocks 24A and 24B may then be removed in the manner described above by installing the additional bone screws 64-68.

The present disclosure includes that contained in the appended claims, as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit of the invention.

Now that the invention has been described, what is claimed is:

1. A bone compression and distraction device for compressing or distracting the ends of a bone, comprising in combination:
    a splint plate including a first and a second hole at one end and a third and a fourth hole at another end, said third hold comprising a slotted hole, said one end of said splint plate being positioned on one end of the bone and said other end of said splint plate being positioned on the other end of the bone;
    a tensioning assembly including a first block seat on one end of said plate and a second block seated on said other end, respectively, of said splint plate and means for adjustably interconnecting said blocks, each said block comprising a transverse hole positioned therethrough;
    first bone/block screw positioned through said transverse hole of said first block and through said first hole of said splint plate and threaded into the one end of the bone;
    second bone screw positioned through said second hole of said split plate into the one end of the bone;
    third bone/block screw positioned through said transverse hole of said second block and through said third hole of said splint plate and threaded into the other end of the bone;
    fourth bone screw for positioning through said fourth hole of said splint plate and threaded into the other end of the bone after said tensioning assembly is operated;
    fifth bone screw for positioning through said first hole in said splint plate and threaded into said one end of the bone after said first bone/block screw and said first block are removed from seated positioning on said splint plate; and
    sixth bone screw for positioning through said third hole in said splint plate and threaded into the other end of the bone after said third bone/block screw and said second block are removed from seated positioning on said splint plate,
    whereby said blocks may be rigidly secured to the respective ends of the bone with said splint plate therebetween and said tensioning assembly operated allowing said third bone/block screw to slide within said third hole of said splint plate to compress or distract the ends of the bone whereupon said fourth bone screw may be installed and then said first and third bone screws are removed with said blocks and replaced with said fifth and sixth bone screws.

2. The device as set forth in claim 1 wherein said tensioning assembly comprises a longitudinal hole positioned in one of said blocks and a longitudinal threaded hole in the other said blocks and a threaded screw slidably inserted through said longitudinal hole and threaded in said longitudinal threaded hole such that rotation of said threaded screw forces said blocks toward each other.

3. The device as set forth in claim 2, further including a threaded hole positioned in each said block and a positioning screw for threaded engagement therewith such that said blocks may be temporarily secured in a space apart position.

4. The device as set forth in claim 2, wherein each said blocks comprises an indentation in a bottom surface thereof facilitating said blocks being seated upon said splint plate.

5. The device as set forth in claim 2, wherein said splint plate comprises another hole at each said end and further including seventh and eighth bone screws positioned for insertion therethrough and threaded into the respective ends of the bone after said fifth and sixth bone screws are installed.

6. The device as set forth in claim 2, wherein an axis of said threaded screw is substantially adjacent to an longitudinal axis of said slotted plate.

7. The device as set forth in claim 1 wherein said tensioning assembly comprises a longitudinal threaded hole in one of the said blocks and a threaded screw threaded through said longitudinal threaded hole whose end pushes against the other said blocks such that rotation of said threaded screw forces said blocks away from each other.

8. The device as set forth in claim 7, further including a blind hole in the other said blocks into which said end of said threaded screw engages.

9. The device as set forth in claim 7, further including a threaded hole positioned in each said block and a positioning screw for threaded engagement therewith such that said blocks may be temporarily secured in a spaced apart position.

10. The device as set forth in claim 7, wherein each said blocks comprises an indentation in a bottom surface thereof facilitating said blocks being seated upon said splint plate.

11. The device as set forth in claim 7, wherein said splint plate comprises another hole at each said end and further including seventh and eighth bone screws positioned for insertion therethrough and threaded into the respective ends of the bone after said fifth and sixth bone screws are installed.

12. The device as set forth in claim 7, wherein an axis of said threaded screw is substantially adjacent to an longitudinal axis of said slotted plate.

* * * * *

UNITED STATES PATENT AND TRADEMARK OFFICE
CERTIFICATE OF CORRECTION

PATENT NO. : 4,929,247
DATED : May 29, 1990
INVENTOR(S) : John M. Rayhack

It is certified that error appears in the above—identified patent and that said Letters Patent is hereby corrected as shown below:

In column 7, line 41, please delete "seat" and insert therefor --seated--.

In column 7, line 43, please delete ", respectively,".

In column 8, line 25, please delete "space" and insert therefor --spaced--.

In column 8, line 39, please delete "slotted" and insert therefor --splint--.

In column 8, line 67, please delete "slotted" and insert therefor --splint--.

Signed and Sealed this

Eleventh Day of June, 1991

Attest:

HARRY F. MANBECK, JR.

Attesting Officer

Commissioner of Patents and Trademarks